US011116560B2

(12) United States Patent
Buchbinder et al.

(10) Patent No.: US 11,116,560 B2
(45) Date of Patent: Sep. 14, 2021

(54) BALLOON CATHETER

(71) Applicant: Cryotherapeutics GmbH, Cologne (DE)

(72) Inventors: Maurice Buchbinder, LaJolla, CA (US); Stewart M. Fox, Cambridgeshire (GB); Domenic Santoianni, Kirkland (CA); Peter Kyone Park, Milpitas, CA (US)

(73) Assignee: Cryotherapeutics GmbH, Cologne (DE)

( * ) Notice: Subject to any disclaimer, the term of this patent is extended or adjusted under 35 U.S.C. 154(b) by 470 days.

(21) Appl. No.: 15/776,156

(22) PCT Filed: Nov. 16, 2016

(86) PCT No.: PCT/EP2016/077823
§ 371 (c)(1),
(2) Date: May 15, 2018

(87) PCT Pub. No.: WO2017/085102
PCT Pub. Date: May 26, 2017

(65) Prior Publication Data
US 2020/0085482 A1 Mar. 19, 2020

Related U.S. Application Data

(60) Provisional application No. 62/255,654, filed on Nov. 16, 2015.

(51) Int. Cl.
*A61B 18/02* (2006.01)
*A61B 34/00* (2016.01)
(Continued)

(52) U.S. Cl.
CPC ........ *A61B 18/02* (2013.01); *A61B 17/12031* (2013.01); *A61B 17/12109* (2013.01);
(Continued)

(58) Field of Classification Search
CPC .......... A61B 18/02; A61B 2017/00292; A61B 2017/00862; A61B 2017/00867;
(Continued)

(56) References Cited

U.S. PATENT DOCUMENTS 8,409,265 B2 * 4/2013 Keller .................... A61F 7/123
607/105
9,060,754 B2 * 6/2015 Buckley ................. A61B 18/02
(Continued)

FOREIGN PATENT DOCUMENTS

WO       2012019156       2/2012
WO   WO 2012/019156       2/2012
(Continued)

OTHER PUBLICATIONS

European Patent Office, International Search Report for Application No. PCT/EP2016/077823, dated Jul. 14, 2017; 6 pps.
(Continued)

*Primary Examiner* — Michael F Peffley
(74) *Attorney, Agent, or Firm* — Sunstein LLP (57) ABSTRACT

A catheter is provided comprising a flexible heat transfer element provided on an outer surface of the catheter. The catheter further comprises a conduit arranged to supply an inflation fluid for inflating the flexible heat transfer element so as to form an inflated balloon, and a plurality of cooling elements arranged to cool the inflation fluid for inflating the balloon. Each cooling element comprises a first tube provided inside a second tube, wherein the first tube is substantially parallel to the second tube. The second tube is configured to receive a flow of a coolant for cooling the cooling element from the first tube.

18 Claims, 5 Drawing Sheets

(51) Int. Cl.
  *A61B 90/00* (2016.01)
  *A61B 17/12* (2006.01)
  *A61B 17/00* (2006.01)
  *A61B 18/00* (2006.01)

(52) U.S. Cl.
  CPC ......... *A61B 17/12136* (2013.01); *A61B 34/25* (2016.02); *A61B 2017/00292* (2013.01); *A61B 2017/00862* (2013.01); *A61B 2017/00867* (2013.01); *A61B 2018/00011* (2013.01); *A61B 2018/00017* (2013.01); *A61B 2018/0019* (2013.01); *A61B 2018/0022* (2013.01); *A61B 2018/00023* (2013.01); *A61B 2018/00166* (2013.01); *A61B 2018/00267* (2013.01); *A61B 2018/00345* (2013.01); *A61B 2018/00577* (2013.01); *A61B 2018/00648* (2013.01); *A61B 2018/00821* (2013.01); *A61B 2018/0212* (2013.01); *A61B 2090/3966* (2016.02)

(58) Field of Classification Search
  CPC ........... A61B 2018/00011; A61B 2018/00017; A61B 2018/00023; A61B 2018/00166; A61B 2018/0022; A61B 2018/00267; A61B 2018/00285; A61B 2018/00345; A61B 2018/00577; A61B 2018/0212; A61B 2018/0262; A61B 2018/0268; A61F 2007/126; A61F 7/123
  See application file for complete search history.

(56) References Cited

U.S. PATENT DOCUMENTS

| | | | |
|---|---|---|---|
| 2011/0184400 A1 | 7/2011 | Pageard | |
| 2013/0345688 A1* | 12/2013 | Babkin | A61B 18/02 606/20 |
| 2016/0249969 A1* | 9/2016 | Santoinanni | A61B 18/02 606/24 |

FOREIGN PATENT DOCUMENTS

| | | | |
|---|---|---|---|
| WO | 2012058153 | 5/2012 | |
| WO | WO 2012/058153 | 5/2012 | |
| WO | 2015067414 | 5/2015 | |
| WO | WO 2015/067414 | 5/2015 | |
| WO | WO-2015067414 A1 * | 5/2015 | ............ A61B 18/02 |

OTHER PUBLICATIONS

International Searching Authority—EPO, International Search Report, PCT/EP2016/077823; dated Jul. 7, 2017. 8 pages.

* cited by examiner

Section A-A

FIG. 8

Section B-B

Section A-A

FIG. 11

Section B-B

BALLOON CATHETER

CROSS-REFERENCE TO RELATED APPLICATIONS

This Application is a U.S. national stage entry under 35 USC § 371 of Patent Cooperation Treaty Application PCT/EP2016/077823, filed Nov. 16, 2016, which claims priority from U.S. Provisional Patent Application 62/255,654, filed Nov. 16, 2015, both of which are incorporated herein by reference in their entireties.

FIELD

The present invention relates to balloon catheters for the invasive treatment of a body. The catheter comprises a plurality of cooling elements which allow fast cooling of the surface of the balloon.

BACKGROUND

From the late 1970s, catheters for cryotherapy have been used in the cardiovascular system starting from, for example, 1977 when it was used to surgically treat cardiac arrhythmias. Over the ensuing years it became widely recognised that cryotherapy was particularly advantageous for working in the heart. Its safety and efficacy was unsurpassed as surgeons were able to ablate delicate cardiac structures such as the A-V node, pulmonary veins and delicate perinodal atrial tissue without concern for thrombosis, perforation or other adverse events.

Another important application for catheters is the treatment of atrial fibrillation. The traditional approach has been to use a catheter having an electrode provided at its tip. The catheter is inserted into a vein, typically in the groin or neck, and threaded up into the heart. The electrode is then used to generate radio waves and create heat, which cauterises the part of the heart tissue so as to prevent the transmission of electrical signals which cause atrial fibrillation. This approach comes with an inherent risk of damaging the oesophagus however, which is located nearby. Thus an alternative method, referred to as cryoablation, has recently grown in popularity, which instead may rely on using a catheter having a cooled balloon at its tip. Once the balloon is inserted and inflated at the ostium of the pulmonary vein, the balloon is cooled significantly so as to destroy the heart tissue that causes atrial fibrillation and restore a normal rhythm to the heart. This technique carries with it a significantly reduced risk of damaging the oesophagus.

A catheter for the treatment of plaque stabilisation by cryotherapy is described in WO 2015/067414 (referred to hereinafter as WO'414). A balloon is inflated around a catheter shaft and subsequently cooled. A co-axially arranged cooling element is used to achieve this, wherein a liquid coolant is conveyed from an inner supply lumen into a larger conduit. When exiting the supply lumen the coolant undergoes a phase change due to the pressure drop which occurs, causing it to evaporate and reduce in temperature. The cold gas is then removed using a return lumen which surrounds the supply lumen in a co-axial manner.

A number of advantages are provided by the above co-axial design, as discussed in WO'414. For example, a single layered balloon may be used since there is little risk of a gas coolant leaking from the catheter. Furthermore cooling occurs, via the phase change, in the location where it is required without the need for insulating layers to be provided. Further still, the cooling element and its supporting lumen may maintain a small cross sectional area, making it suitable for applications in small diameter arteries. WO'414 discloses the use of the catheter for cryotherapy in small arteries and so attempts to provide a catheter shaft having smallest possible diameter to it (which is typically less than 1.5 mm). This catheter shaft envelopes the co-axial cooling element, a guide wire lumen and a conduit configured to inflate and deflate the balloon. These lumens are assembled so as to reduce the overall diameter of the shaft.

SUMMARY OF THE INVENTION

In accordance with an aspect of the invention, there is provided a catheter comprising:

a flexible heat transfer element provided on an outer surface of the catheter;

a conduit arranged to supply an inflation fluid for inflating the flexible heat transfer element so as to form an inflated balloon; and a plurality of cooling elements arranged to cool said inflation fluid for inflating the balloon;

wherein each cooling element comprises a first tube provided inside a second tube, wherein the first tube is substantially parallel to the second tube; and the second tube is configured to receive a flow of a coolant for cooling the cooling element from the first tube.

Preferably, the cooling elements are arranged within the catheter so that the inner surface of the balloon is cooled substantially uniformly.

Preferably, said cooling elements are elongate and arranged parallel to one another.

Preferably, each cooling element has substantially the same lateral spacing from an axis of the balloon parallel to the cooling tubes.

Preferably, as viewed in the plane normal to the longitudinal axis of the cooling elements and relative to the centre of the balloon, each of a plurality of the cooling elements is separated from an adjacent cooling element by a substantially equal angle.

Preferably, said cooling elements are configured such that, when the flexible heat transfer element is inflated, the spacing between the cooling elements is larger than when the balloon is not inflated.

Preferably, said plurality of cooling elements comprises at east three cooling elements.

Preferably, said catheter is a perfusion catheter further comprising a central perfusion lumen configured to convey a bodily fluid along the centre of the catheter, wherein said cooling elements are arranged around said perfusion lumen.

Preferably, when in use in a vessel, the inflated flexible heat transfer element occludes fluid flow between the walls of the vessel and the inflated flexible heat transfer element.

Preferably, said plurality of cooling elements is provided inside the flexible heat transfer element.

Preferably, when in use, the first tube and the second tube are operated such that the pressure of the second tube is lower than the first tube.

Preferably, each cooling element comprises an elongate cooling chamber configured to receive coolant from the first tube and provide said coolant to the second tube.

Preferably, for each cooling element, the elongate cooling chamber is arranged co-linearly with an end of the second tube.

Preferably, each cooling element further comprises a restriction tube configured to convey the coolant from the first tube to the cooling chamber, wherein said restriction tube has narrower internal diameter than the first tube.

Preferably, the restriction tube and cooling chamber are configured such that when the coolant conveyed along the first tube as a liquid, at least some of the coolant undergoes a phase change in the restriction tube and/or in the cooling chamber and returns through the second tube as a gas.

Preferably, the conduit is further configured to provide a return flow of the inflation fluid of the flexible heat transfer element.

Preferably, the conduit comprises a third tube for providing a supply and/or return flow of the inflation fluid of the flexible heat transfer element; and the conduit comprises a fourth tube for providing a supply and/or return flow of the inflation fluid of the flexible heat transfer element.

Preferably, the catheter further comprises a guide wire lumen.

Preferably, each of the cooling elements is not attached to the end of the guide wire lumen and wherein each cooling element is configured such that, when in use, the flow of the coolant causes the cooling element to vibrate.

Preferably, the flexible heat transfer element has single walled outer membrane.

Preferably, the catheter further comprises a heater for heating the inflation fluid, or solidified inflation fluid, of the flexible heat transfer element.

Preferably, each cooling element is substantially linear and arranged to be substantially parallel with the longitudinal axis of the catheter when the balloon is inflated.

Preferably, each cooling element is configured such that, when the balloon is inflated, each cooling element is configured to at least partially have a helical shape.

Preferably, when the balloon is inflated, each cooling element is configured so that it is spaced apart from the surface of the flexible heat transfer element.

Preferably, the catheter further comprises a plurality of said flexible heat transfer elements;

wherein each flexible heat transfer element is configured to be inflated into a respective balloon; and wherein each balloon contains one of said cooling elements.

Preferably, said balloons are in thermal communication with each other.

Preferably, the catheter further comprises an elasticated member that extends around said flexible heat transfer elements so as to hold said balloons together.

In accordance with another aspect of the invention, there is provided a catheter comprising:

a plurality of heat transfer elements, wherein each heat transfer element flexible and is configured to be inflated with an inflation fluid so as to form a respective cooling element balloon;

wherein each cooling element balloon comprises a cooling element arranged to cool said inflation fluid.

Preferably, each cooling element comprises a first tube provided inside a second tube, wherein the first tube is substantially parallel to the second tube; and the second tube is configured to receive a flow of a coolant for cooling the cooling element from the first tube.

Preferably, the catheter further comprises an elasticated member that extends around said flexible heat transfer elements so as to hold said cooling element balloons together.

LIST OF FIGURES

Embodiments of the invention will now be discussed with reference to the accompanying drawings in which.

DESCRIPTION OF EMBODIMENTS

The catheter design of WO'414 experiences a problem. Only one cooling element is provided, which is provided substantially in the centre of the balloon. If the size of the balloon is increased, for example where the catheter is intended for use in larger arteries, it can therefore take a substantial amount of time for the cooling applied by the cooling element to reach the surface of the balloon, and therefore the surrounding tissue.

Embodiments of the invention provide a new and advantageous design of balloon catheter. The new design of catheter comprises a plurality of cooling elements. This increases the cooling power provided to the catheter balloon. Furthermore by providing a plurality of cooling elements, spatial variations in heat transfer are reduced. Further still, advantages of the cooling elements disclosed in WO'414 are retained whilst allowing a larger catheter to be created which is more appropriate for treating atrial fibrillation. The catheter design has a wide range of applications that may include cryotherapy, the treatment of renal denervation and tumour ablation.

Multiple different arrangements can be used to reduce the spatial variations in heat transfer across the balloon and in general this will depend on the shape of the inflated balloon and the size and number of lumens provided. Furthermore, different cooling elements could have different sizes, or be operated differently, and so cool the balloon at different rates. However, the cooling elements are preferably arranged and operated to provide substantially uniform cooling to the surface of the balloon. In other words, the cooling elements are preferably arranged to provide a substantially even cooling distribution across the inflated balloon and ensure that the entire perimeter of the balloon is cooled at the same rate.

The catheter is a balloon catheter and comprises a plurality of lumens supported inside a shaft, except for in a balloon region where they are instead provided within a flexible heat transfer element which is configured to be inflated to form a balloon. One or more lumens are provided inside the flexible heat transfer element for providing a supply and return of inflation fluid to the balloon, as well as a plurality of cooling elements for cooling the inflation fluid.

Each cooling element is elongate, substantially cylindrical and comprises tubular walls. Each cooling element also comprises first and second tubes for providing supply and return paths of a coolant, wherein the first tube (which is also referred to herein as the supply lumen) is provided inside a larger second tube (which is also referred to herein as the return lumen). The first tube and the second tube are each elongate and extend along axes that are substantially parallel to one another. The distal tip of the return lumen may be closed, whereas the distal tip of the supply lumen may be open and stop short of the end of the return lumen such that coolant may flow from the supply lumen in a first direction into the return lumen, and then flow in a second direction, opposite to the first direction, back along the return lumen. When the coolant flows from the supply lumen to the return lumen it moves into a region of increased volume and consequently reduces in pressure. This causes a phase change in the coolant, wherein at least some of the coolant will liquefy, causing the temperature of the cooling element to reduce.

The one or more lumens that provide supply and return flows of a fluid for inflating the balloon are completely separate from the lumens used to supply the coolant. The inflation of the balloon and the cooling of the cooling element are performed by separate mechanisms and these operations can be controlled and operated independently of each other.

The catheter may also contain a means for heating the inflation fluid within the balloon. This would be used, for example, if the inflation fluid froze during treatment and it was necessary to rapidly thaw the inflation fluid. The ability to induce such rapid thawing is particularly beneficial in case the catheter needs to be removed from an artery quickly, for example in emergency situations. The heat could be provided by any type of heater, for example a small electric heater, such as a resistor, positioned inside the balloon but outside the cooling element and supplied by an electric current via wires running down the catheter shaft. The heater element could be formed by a thin film resistor printed on the outer surface of the cooling element, a discrete resistor positioned inside the balloon, or by the inflation fluid itself. In the case where the inflation fluid forms the heater element, wires would supply electricity to electrodes at the proximal and distal ends of the balloon and terminate there, in contact with the inflation fluid, so that an AC or DC current could be passed through the inflation fluid inside the balloon, causing it to warm up.

In use, the catheter is inserted into a body such that the balloon region is positioned next to a region of tissue to be cooled in a vessel. For example in the event that the catheter is used to treat atrial fibrillation, this tissue may be the part of the pulmonary vein which causes the heart to beat irregularly. If the catheter is used instead for plaque stabilisation by cryotherapy, the balloon region may be positioned next to the plaque. The catheter's balloon is inflated by a liquid and the outer surface of the balloon comes into thermal contact with the tissue. Coolant is supplied to the cooling elements and the temperature of the cooling elements reduces. The inflation liquid within the balloon contacts the outer surface of the cooling elements and is thereby cooled and may solidify.

An advantageous aspect of the above-described catheter design is that the coolant of the cooling element is not the same as the fluid used to inflate the balloon. The cooling element can safely support a phase change of the coolant since the cooling elements are closed. Since the coolant is not in fluid communication with the inflatable flexible heat transfer membrane, there is little chance of it leaking from the catheter into a blood vessel and so the requirement to have a double layered balloon may be avoided. A single layered balloon is significantly more maneuverable and streamlined than a balloon with multiple membranes. Moreover, the catheter design is simpler than known designs employing a double balloon system and this reduces costs and manufacturing complexity. In some embodiments, multiple balloons may be provided however.

The arrangement of the coolant supply lumen inside the coolant return lumen allows for the cooling element to maintain a small cross sectional area. This means that multiple cooling elements may be provided within the catheter. A higher number of cooling elements may cool the balloon faster and more evenly. The upper limit of the number of cooling elements that may be provided may depend on the size of the blood vessel which the catheter is designed to be inserted into, and on how small each cooling element can be manufactured to.

A further benefit of the cooling element design is that cooling due to the phase change occurs in a clearly defined location that can be controlled as required. This improves the efficiency of the catheter system since the lumens that deliver coolant do not need to have high levels of insulation between the coolant and the surrounding environment. Moreover, the parallel arrangement of supply and return lumens means that the liquid coolant is kept cool by the cold, gaseous coolant returning from the distal tip of the catheter. This prevents the liquid coolant from boiling as it flows into that part of the catheter which is inside the body (and therefore at 37° C.).

In order for the tissue to be cooled as quickly as possible, it is advantageous to position the cooling elements close to the inner surface of the balloon (i.e. the flexible heat transfer element). This is a significant departure from the WO'414, which only discloses one co-axial cooling element, wherein this cooling element extends substantially along the centre of the balloon. In order to achieve uniform cooling of the balloon inflation fluid it is desirable for the cooling elements not to contact the flexible heat transfer element itself. It is therefore advantageous for the cooling elements to extend towards and along the surface of the balloon, whilst being separated from the inner surface of the balloon itself. This can be achieved by the cooling elements extending both radially outward from a central axis of the catheter, and along said axis. Typically the central axis is occupied by a guide wire lumen.

Further advantages of embodiments are set out in the detailed description provided below.

Figure 1:
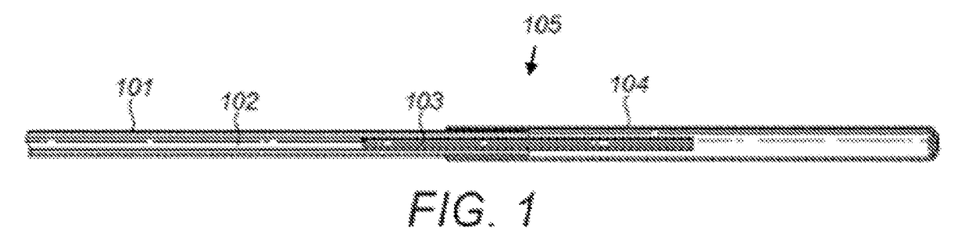
FIG. 1 is a schematic illustration of a cross section of a cooling element of a catheter according to an embodiment.

FIG. 1 shows a cross section of the design of a cooling element 105 of a catheter according to an embodiment. On the left hand side of FIG. 1 are shown the tubular supply lumen 102 and the tubular return lumen 101 of the coolant. The supply lumen 102 is positioned inside the return lumen 101 in a substantially co-axial configuration. An end of the supply lumen 102 is connected to, and in fluid communication with, a restriction tube 103. The restriction tube 103 has a narrower diameter than the supply lumen 102. The end of the return lumen 101 that is not connected to the supply lumen 102 ends in a cylindrical cooling chamber 104 of cooling element 105. In the present embodiment, the cooling chamber 104 has a slightly larger diameter than the return lumen 101 and extends over the outside of the return lumen 101.

In use, a flow of pressurised coolant is input to the supply lumen 102. The coolant may be a liquid or a mixture of a liquid and a gaseous form of the coolant. The restriction tube 103 at the end of the supply lumen 102 ensures that there is little pressure drop within the supply lumen 102 and so most, or all, of the pressurised liquid coolant remains in the liquid phase in the supply lumen 102. Along the length of the restriction tube 103, the pressure drops from a maximum value at the connection to the supply lumen 102 to a lower pressure at the exit of the restriction tube 103 into the cooling chamber 104. When the liquid coolant flows into the restriction tube 103 the pressure drop caused by the restriction means that the pressure of the liquid falls below its vapour pressure at the temperature of its surroundings at that point. This causes at least some of the liquid coolant to evaporate and undergo a phase change into a gas. Liquid coolant that flows from the restriction tube 103 into the cooling chamber 104 will also expand and may evaporate within the cooling chamber 104 and/or return lumen 101. The expansion of the coolant, and the phase change of the coolant, has a cooling effect on the walls of the cooling chamber 104. The coolant then flows from the cooling chamber 104, in liquid and/or gaseous form, through the return lumen 101. The pressure within the return lumen 101, and thereby the cooling chamber 104, is preferably reduced by a vacuum pump. The vacuum pump, described in more detail later, operates on the end of the return lumen 101 that is not connected to the cooling element 105. The reduction of pressure both increases the cooling effect due to expansion and phase change of the coolant and ensures that the coolant in the cooling chamber 104 flows into the return lumen 101.

Figure 2:
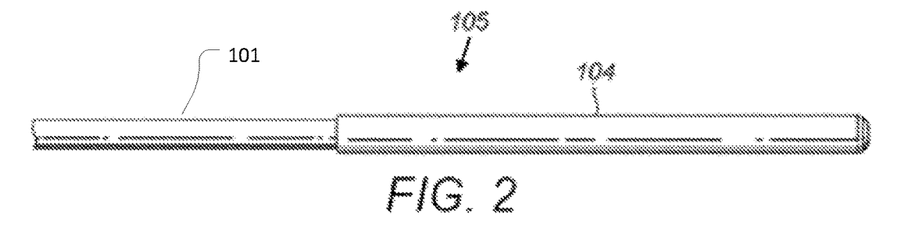
FIG. 2 is a schematic illustration of a cooling element of a catheter according to an embodiment.

FIG. 2 shows a perspective of the cooling element 105 of FIG. 1. The cooling chamber 104 has a slightly larger diameter than the return lumen 101. A greater cooling effect is achieved since more coolant will undergo a phase change in the cooling chamber 104. In addition, the outer diameter of the cooling chamber 104 has a larger surface area and is therefore more effective at cooling the inflation fluid.

Preferably the lumens of the cooling element are made of reasonably strong materials so that they can withstand the pressure of a pressurised coolant. In some embodiments these lumens also have a degree of flexibility so that the catheter can deform to match the profile of an artery.

The supply lumen 102, return lumen 101 and restriction tube 103 may be made of nylon, tri-layered tubing, polyimide, PEBAX™, such as PEBAX 55D, or other suitable materials. The restriction tube 103 and supply lumen 102 may be made at the same time so that they are integral with each other, or they may be constructed as separate components and then glued together. Furthermore the cooling chamber 104 may be made entirely, or in part, of copper so that the cooling chamber 104 has good thermal conductivity properties. Alternatively, the entire of the cooling element 105 may be made from polyimide, as this material is strong, enabling the walls to be made extremely thin. Using the same material throughout the cooling element 105 also improves the ease of manufacture of said cooling elements.

Preferably, the coolant is $N_2O$ and enters the restriction tube 103 with substantially all of the coolant being in the liquid phase. The coolant may exit the restriction tube 103 with some of the $N_2O$ being in the liquid phase and some of the $N_2O$ being in the gas phase. Preferably, most of the $N_2O$ is in the liquid phase.

Figure 3:
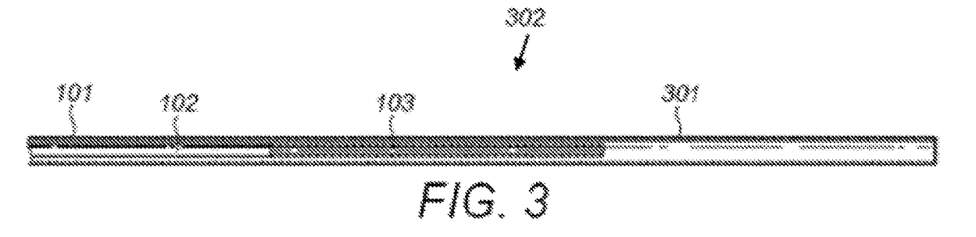
FIG. 3 is a schematic illustration of a cross section of a cooling element of a catheter according to an embodiment.

The embodiment shown in FIG. 3 differs from that shown in FIG. 1 in that the cooling chamber 301 of the cooling element 302 has the same inner and outer diameters as the return lumen 101. The cooling chamber 301 is still closed, i.e. blocked, at the other end to that connected to the return lumen 101. The dimensions and materials of the return lumen 101, supply lumen 102 and restriction tube 103 may be the same as described above with reference to FIGS. 1 and 2. The length of the cooling chamber 301 from the end of the restriction tube 103 to the closed end of the cooling chamber 301 is preferably 1 mm to 15 mm. Advantageously, the cooling chamber 301 is narrower than that shown in FIGS. 1 and 2.

The presence of a restriction tube 103 and a distinct cooling chamber 104 is optional however. In alternative embodiments, the liquid coolant may flow directly from the supply lumen 102, into the return lumen 101, either through the distal tip (i.e. end) of the supply lumen 102 or through one or more apertures in the wall of supply lumen 102, distributed along its length. In this case, some of the coolant may undergo a phase change when moving to enter the return lumen 101, which has a lower pressure than the supply lumen 102. This lower pressure may be achieved by ensuring that the annular internal volume of the return lumen 101 is larger than the internal volume of the supply lumen 102 and/or by using a vacuum pump.

The array of cooling elements is provided within an inflatable heat transfer membrane 16 that is configured to be inflated into a balloon 70. The cooling elements are arranged such that, when the balloon 70 is inflated, a substantially even cooling distribution is applied across the balloon 70. In particular it is desirable that the outside of the balloon 70 (i.e. the surface of the inflatable heat transfer membrane 16) is cooled quickly and uniformly. This may be achieved in a number of different ways, examples of which will be discussed below.

Co-ordinate axes are provided in FIGS. 4 to 12 for reference. In each case the abscissa x-axis extends along the central (i.e. longitudinal) axis of the catheter, whilst the ordinate y-axis and the z-axis extend a transverse plane. The y-axis and the z-axis are perpendicular to the x-axis and are mutually perpendicular to one another.

Figure 4:
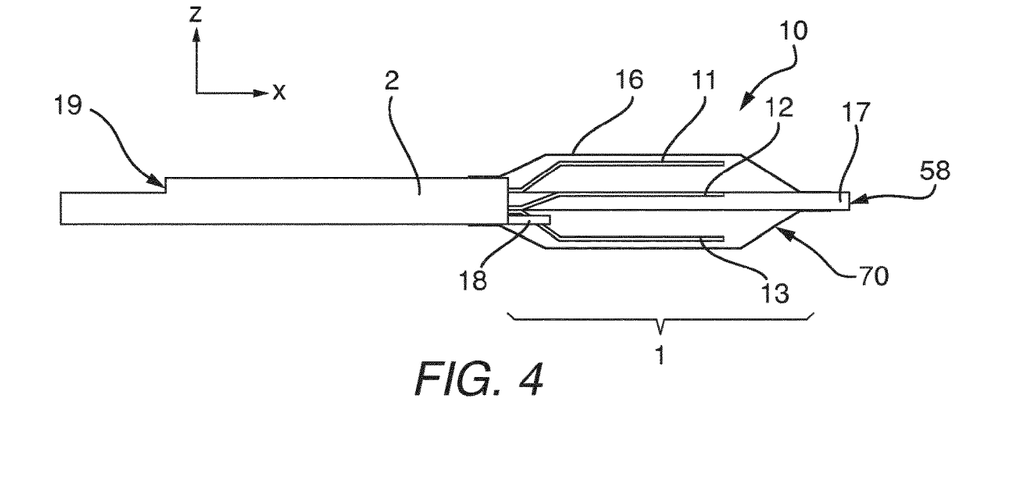
FIG. 4 is a schematic illustration of a catheter according to an embodiment.

FIG. 4 is a perspective view of a catheter 10 according to an embodiment. The catheter 10 comprises a hollow tubular shaft 2 which extends along the length of the catheter and envelops the lumens provided within except in a balloon region 1, where an inflatable flexible heat transfer member 16 is provided. The shaft 2 is made of polyether block amide as braided, or unbraided, PEBAX™, such as PEBAX 55D, and is formed using a heat reflow process.

The interior of the shaft 2 comprises a conduit 18 and a plurality of elongate, cylindrical cooling elements 11, 12, 13 which are each arranged around a cylindrical guide wire lumen (GWL) 17. The cooling elements 11, 12, 13 may be similar to any of the previous embodiments described and each comprise a supply lumen provided inside a return lumen.

The GWL 17 is configured to be threaded over a surgically implanted guide wire, when in use, for positioning the catheter 10 inside a patient. The GWL 17 extends from the guide wire entrance aperture 58 at the distal tip of the catheter 10, to a guide wire exit aperture 19 provided on the shaft 2 (as is standard for Rapid Exchange catheters). Alternatively, an 'over the wire' configuration may be used. The GWL 17 is a hollow tube and is made of tri-layer or a similar material.

The inflatable heat transfer membrane 16 is adhered to the distal tip of the shaft 2 on its proximal end and the GWL 17 on its distal end. The region between these two ends is configured to be inflated into a substantially elongate, cylindrical balloon 70. Embodiments also include the inflated balloon alternatively being substantially spherical. The conduit 18 (referred to herein as the inflation lumen) is provided for supplying an inflation fluid for inflating the flexible heat transfer element 16 so as to form the inflated balloon 70. The inflation lumen 18 extends along the inside of the shaft 2, and in this embodiment, protrudes from the shaft 2 into the balloon region 1. Alternatively however the inflation lumen may terminate at the end of the shaft 2. In some embodiments a plurality of said inflation lumens may be provided in order to allow faster inflation or to reduce the overall cross sectional area of the shaft 4 since in some instance two or more small inflation lumens may be physically easier to accommodate inside the shaft 2 than one large inflation lumen.

The shaft 2, and in particular, the space between the lumens provided inside the shaft 2, may act as a return path for providing a flow of inflation fluid from the balloon 70 back along the shaft 2 in a reverse direction to the flow of inflation fluid in the inflation lumen 18. This enables space savings inside the shaft 2 since it is not necessary to provide a separate deflation tube. Alternatively, the flow direction of the inflation fluid may be reversed such that the conduit 18 behaves as a deflation lumen whilst the shaft 2 behaves as an inflation lumen. Furthermore the shaft 2 and/or inflation lumen 18 may function as both an inflation and deflation lumen in some circumstances, in which case the pressure is simply reversed at one end of the shaft 2 and/or inflation lumen 18.

Only three cooling elements 11, 12, 13 are visible in FIG. 4, although four cooling elements are in fact provided in this embodiment. The cooling elements 11, 12, 13 are not attached to the GWL 17 inside the balloon region 1 and so the cooling chambers are therefore free to vibrate, i.e. move laterally with respect to the longitudinal axis of the GWL 17.

The closed distal end of the return lumen may typically extend approximately an additional 2.0 to 3.0 mm from the open distal end of the supply lumen. This region could be thought of as the cooling chamber 104.

The following dimensions may be desirable for certain applications that may include the treatment of atrial fibrillation on a human or animal:
  Cooling element 11, 12, 13
    Outer diameter=0.35 to 1.0 mm
    Outer wall thickness=0.019 to 0.05 mm
    Length=15 to 30 mm
  Return lumen 101
    Outer diameter=0.35 to 1.0 mm
    Outer wall thickness=0.019 to 0.05 mm
    Length=1000 to 1750 mm
  Supply lumen 102
    Outer diameter=0.12 to 0.4 mm
    Outer wall thickness=0.014 to 0.05 mm
    Length=1000 to 1750 mm
  Restriction tube 103
    Outer diameter=0.0762 to 0.140 mm
    Outer wall thickness=0.019 to 0.0254 mm
    Length=5 to 50.8 mm
  Inflation lumen 18
    Outer diameter=0.254 to 0.406 mm
    Outer wall thickness=0.0191 to 0.0508 mm
    Length=1000 to 1750 mm
  GWL 17
    Outer diameter=0.45 to 1.0 mm
    Inner diameter=0.40 to 0.95 mm
    Length=650 mm
  Shaft 2
    Diameter=1.35 to 3.3 mm Embodiments also include other dimensions, in particular the dimensions as provided in WO'414 which are incorporated herein by reference.

The cooling elements 11, 12, 13 are encompassed by the balloon 70. That is to say, in use the cooling elements 11, 12, 13 are within the inflation fluid of the balloon 70 and there is no outer membrane of the balloon 70 arranged between the inflation fluid and the cooling elements 11, 12, 13.

The balloon 70 is typically 15 mm to 30 mm long and, when deflated, is preferably substantially flush with the outer surface of the shaft 2 so that the outer diameter of the catheter is not increased by the deflated balloon. For example, the outer diameter of the catheter may be substantially 4 Fr. When inflated, the outer diameter of the balloon 70 may be 2.5 mm to 4 mm. A larger balloon 70 may be required in the treatment of atrial fibrillation however with a diameter of approximately 24 mm (e.g. +1-10%). The dimensions of the catheter components, such as the lumen, may be adjusted depending on the application and, in particular, the size which the balloon is configured to be inflated to. For example, larger lumen may be desired in order to inflate and deflate a large balloon more quickly, or apply an increased cooling effect.

The balloon 70 may be made of a variety of materials and is desirably compliant or semi-compliant to ensure a good fit with the target area for effective heat exchange and a more even temperature distribution around the tissue. The balloon 70 may also be non-compliant if this is appropriate for the desired application. The balloon design and construction may be as known in the art of balloon angioplasty. However, there is no need for the balloons to be as strong, and with as thick membranes, as those used for angioplasty since the inflation pressures used in embodiments are substantially lower than those used in angioplasty. This is because the balloons are not required to enlarge the vessel. The balloons in embodiments are only required to make a good thermal contact with the vessel and the balloons are therefore preferably made with a thinner membrane than balloons used for angioplasty. The balloons can be made of a variety of materials such as silicone or polyurethane for compliant balloons and nylon or polyester for non-complaint balloons. Wall thickness will also vary depending on the properties to be achieved and are generally in the range of 5 to 100 microns. The balloon may also have a substantially smooth exterior surface so that heat transfer is optimised from the tissue on the interior surface of the vessel. The balloon material and thickness may be optimised to minimize the thermal gradient across the balloon surface.

In use, an inflation fluid is supplied to the inflation lumen 18 to inflate the balloon 70. The cooling elements 11, 12, 13 are then cooled by the expansion and/or evaporation of the coolant as described in the above embodiments. The flow of the coolant that may be a liquid and/or gas, from the supply lumen 102 to the return lumen 102 (potentially via a restriction lumen and cooling chamber, if provided) causes the distal end of the cooling elements, which is not fixed to the GWL 17, to vibrate. Advantageously, this vibration movement of the cooling element 105 increases the amount of flow of the inflation fluid over and around the cooling chambers 104 and thereby both increases the rate at which the inflation fluid is cooled and the temperature uniformity of the inflation fluid. The inflation fluid is in contact with the inner surface of the balloon 70 and the balloon 70 is thereby cooled as the inflation fluid is cooled. The outer surface of the balloon 70 is therefore cooled due to the cooling of the inflation fluid by the cooling element. When an operator determines that sufficient cooling has been applied by the catheter, the balloon 70 is deflated using the deflation lumen and the catheter can then be removed.

Preferably the inflation fluid has a fixed volume. This limits any damage caused by any leakage of the inflation fluid from the catheter. Any leakage of the inflation fluid can also be detected by monitoring the pressure of the inflation fluid when the balloon 70 is inflated or by determining if the amount of inflation fluid after a procedure is the same as that at the start of the procedure.

The inflation fluid is preferably a liquid so that even if there is a leakage from the catheter, the leakage is of a liquid and not a gas. The inflation fluid may be a solution that comprises sodium chloride, such as saline, with a sodium chloride concentration of about 0.9%, or a solution with a higher concentration of sodium chloride, preferably a 25% concentration of sodium chloride. The inflation fluid is preferably water based, and may include various additives to lower the freezing point. Additives may include one or more of sodium chloride, calcium chloride, ammonia, ethanol, propylene glycol, ethylene glycol, propanone and butanone. Other additives may also be used. The inflation fluid is also preferably sterile. To ensure that the inflation fluid is sterile, the inflation fluid may be provided from a separate container, such as a pre-packed bag or syringe that is connected to the catheter.

The same apparatus for supplying the inflation fluid to into the inflation lumen 18 may have its operation reversed so that it is also able to deflate the balloon 70 by removing the inflation fluid. For example the inflation fluid may be injected into the lumen 18 by an operator pressing on the plunger of a syringe. The same syringe can also be used to remove the inflation fluid by the operator withdrawing the plunger. Advantageously, such an arrangement allows an operator to easily determine if any of the inflation fluid has leaked from the catheter by checking how much inflation fluid is in the syringe after the balloon 70 has been deflated.

The catheter could alternatively be realised with the cooling elements 11, 12, 13 being fixed to the GWL 17. However, this prevents the cooling elements 11, 12, 13 from vibrating and so the cooling of the inflation fluid is slower.

In order to cool the perimeter of the balloon 70 and, in particular, the flexible heat transfer membrane 16 and any surrounding tissue, as quickly as possible it is advantageous for the cooling elements 11, 12, 13 to protrude outwards from the shaft 2 towards and along the surface of the inflated flexible heat transfer membrane 16 so as to effectively trace the surface of the balloon 70 along the x-axis. The cooling elements 11, 12, 13 are symmetrically arranged inside the balloon 70 and in this case are radially dispersed by 90 degrees from one another around the central GWL 17. This ensures that the balloon 70 is cooled evenly around its outer surface and would be extremely difficult to achieve, for example, if only one cooling element was provided on one side of the balloon 70.

In the embodiment shown in FIG. 4, when inflated, the cooling elements extend from the shaft 2 in a direction perpendicular to the longitudinal axis of the catheter 10, remaining substantially parallel to the longitudinal axis, until they are either touching, or preferably separated from the inner surface of the flexible heat transfer membrane 16 by approximately 0.1 to 5 mm. Preferably, the separation is 0.1 to 2.5 mm or 0.1 to 1.5 mm, depending on the application and, in particular, the diameter of the inflated balloon.

The cooling elements then extend along the longitudinal axis of the balloon 16 only until they terminate approximately midway along the distal half of the balloon region 1. This shape can be achieved by preforming the cooling elements 11, 12, 13 such that they naturally assume a desired shape when the balloon 70 is inflated. The cooling elements 11, 12, 13 each have an intrinsic mechanical bias which causes them to flex outwards in a radial direction during inflation of the balloon 70. When the flexible heat transfer membrane 16 has not yet been inflated, the force applied by the external pressure acting inwards on the balloon region 1 and/or the force required to expand the membrane of the balloon overcomes the mechanical bias of the cooling elements 11, 12, 13 and the cooling elements 11, 12, 13 extend along the longitudinal axis of the catheter 10 only. During inflation however, as the volume of the balloon 70 is increased, the inward force acting on the cooling elements 11, 12, 13 is reduced which enables them to extend outwards towards the perimeter of the balloon 70. Initially therefore, as the balloon 70 is being inflated, an outer surface of the cooling elements 11, 12, 13 may abut against the inner surface of the flexible heat transfer membrane 16, until the balloon 70 is inflated beyond the point at which no net force is applied to the cooling elements 11, 12, 13. At this stage the cooling elements 11, 12, 13 may be separated from the flexible heat transfer membrane 70 by a small gap filled with inflation fluid. This is shown in FIG. 4.

Alternatively, instead of preforming the cooling elements 11, 12, 13 with intrinsic mechanical bias, each cooling element 11, 12, 13 could be mounted to (e.g. glued or threaded through) an elastic basket, for example formed of nitinol. This basket may have a mechanical bias so as to assume a desired shape inside the inflated balloon 70 which matches that of the balloon 70, albeit at a fractionally smaller volume.

In order for the cooling elements to assume the above configurations, it is desirable for them to be constructed of a flexible material which is elastically deformable, such as polyimide.

Figure 5:
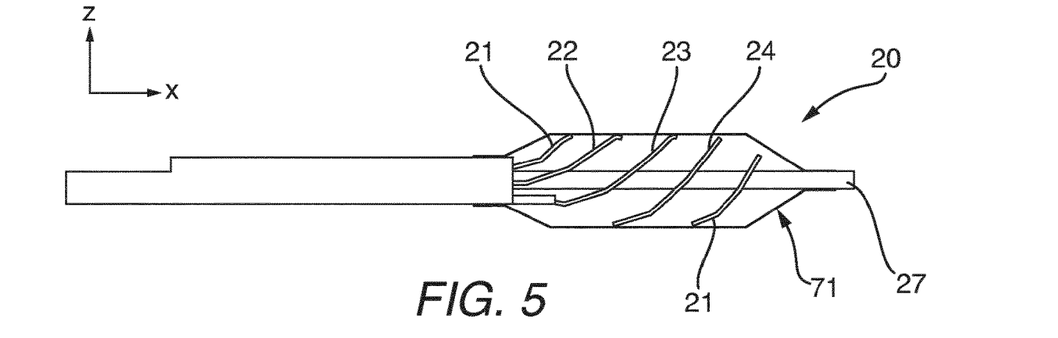
FIG. 5 is a schematic illustration of a catheter according to an embodiment.

A further embodiment of a catheter 20 is shown in FIG. 5, which has substantially the same features as the embodiment of FIG. 4 except that the cooling elements 21, 22, 23, 24 extend around the GWL 27 in a helical pattern. Each cooling element 21, 22, 23, 24 extends along the x, y and z axes inside the balloon 71 so as to form a complete ring that extends around the circumference of the balloon 71. Once again the cooling elements 21, 22, 23, 24 may be mounted to an elastic basket or preformed so as to assume this configuration when the balloon 71 is inflated. This embodiment provides improved uniformity to the cooling across the surface of the balloon 71, which is particularly advantageous for example in the treatment of atrial fibrillation.

Figure 6:
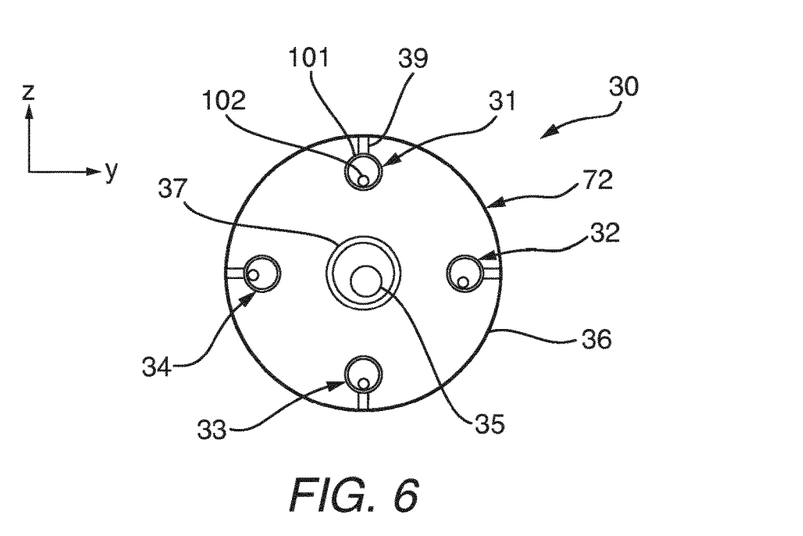
FIG. 6 is a schematic illustration of a cross section of a catheter according to an embodiment.

A further embodiment is shown in FIG. 6, wherein a cross sectional view has been taken through the transverse plane of the balloon 72. This embodiment substantially matches the previous embodiments of FIGS. 4 and 5. For example, four cooling elements 31, 32, 33, 34 are symmetrically arranged around a central GWL 37 which encases a guide wire 35. In a first cooling element 31, the cross sectional view clearly illustrates a supply lumen 102 arranged inside a return lumen 101 (each of which extend primarily along the x-axis. FIG. 6 also shows that the volume of the return lumen 101 is substantially larger than that of the supply lumen, meaning that the pressure of the gas will decrease when it flows from the supply lumen 102 to the return lumen 101, as previously described. This embodiment differs from the previous embodiments described however in that an outer surface of each of the cooling elements 31, 32, 33, 34 is mounted to the flexible heat transfer member 36 either partially or fully along the longitudinal axis of said cooling elements 31, 32, 33, 34. In order to improve the uniformity of the cooling applied by the cooling elements 31, 32, 33, 34 across the surface of the flexible heat transfer member 39, each of the cooling elements 31, 32, 33, 34 is adhered to an attachment member, which may have a poor thermal conductivity, that separates the outer surface of the cooling elements 31, 32, 33, 34 from the inner surface of the balloon 72. Alternatively the cooling elements 31, 32, 33, 34 may be adhered directly to the inside of the balloon. This method ensures that the cooling elements 31, 32, 33, 34 assume the desired configuration when the balloon 72 is inflated and is equally applicable to the previous embodiments described.

A problem exists when implementing perfusion, in particular with cryotherapy, in that the heat from the perfused fluid (which is typically at around 37 degrees Celsius) heats the inflation fluid of the catheter balloon, thereby reducing the cooling effect on the tissue. Furthermore, the existence of a perfusion lumen can lead to uneven cooling around the outside of the balloon. These problems are solved, or at least reduced, by the following embodiments, wherein multiple cooling elements, each comprising a supply lumen provided inside a return lumen, surround a perfusion lumen of the catheter.

It is advantageous to provide a heat sink between the perfusion lumen and the cooling elements so as to form a barrier to reduce the heating effect that the warm blood flowing through the perfusion lumen could have on both the cooling elements and the flexible heat transfer membrane. In the following embodiments this is achieved by providing a volume of fluid with poor thermal conductivity, such as a gas, between the perfusion lumen and the inflation fluid to be cooled by the cooling elements (which is typically a liquid).

Figure 7:
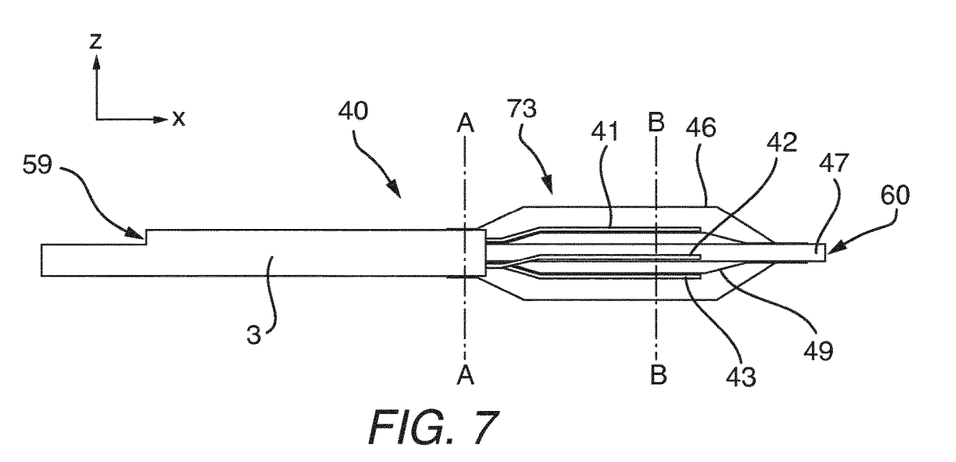
FIG. 7 is a schematic illustration of a perfusion catheter according to an embodiment.

FIG. 7 shows a perspective view of a further embodiment of a catheter 40. This embodiment is substantially similar to the embodiment of FIG. 4 except that two balloons are provided. The GWL 47 is configured to be threaded over a guide wire 45 as before, however in this embodiment the GWL 47 also functions as a perfusion lumen which is configured to convey a blood from the guide wire exit aperture 59 to the guide wire entrance aperture 60 when in use. This feature is optional however as the catheter 40 may alternatively be used without perfusion in some embodiments, in which case the GWL 47 will be provided to engage with a guide wire 45 only.

An inner balloon 49 is inflated inside an outer balloon 46 in a co-axial configuration about a common longitudinal axis, which extends along the GWL 47. Both the inner balloon 49 and the outer balloon 46 are formed of a similar inflatable flexible membrane, however in some examples the thermal conductivity of the flexible membrane of the inner balloon 49 may advantageously be less than that of the outer balloon 46. A plurality of cooling elements 41, 42, 43, 44 are provided inside the outer balloon 46 and extend along the outer surface of the inner balloon 49 in a predetermined configuration. This is preferably achieved by adhering an outer edge of the cooling elements 41, 42, 43, 44 to the outside of the inner balloon 49, but may alternatively be achieved using any of the previous techniques discussed, for example by preforming said cooling elements 41, 42, 43, 44 with a mechanical bias.

The inner balloon 49 is preferably inflated using a gas such as air or nitrogen, whereas the outer balloon 73 is preferably inflated using a sterile liquid, such as saline. It is advantageous to fill the outer balloon 73 with a liquid since this will reduce the likelihood of gas escaping from the catheter into the blood of a patient if any of the lumens or membranes inside the catheter 40 rupture. Furthermore, liquids are more thermally conductive than gases, meaning that the cooling elements 41, 42, 43, 44 may more efficiently cool the outer flexible heat transfer membrane 46.

Figure 8:
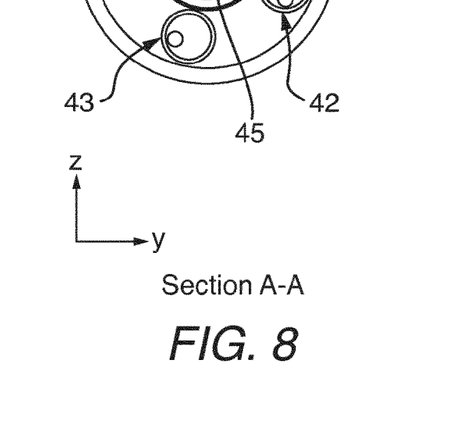
FIG. 8 is a schematic illustration of a cross section of a perfusion catheter according to an embodiment.
Figure 9:
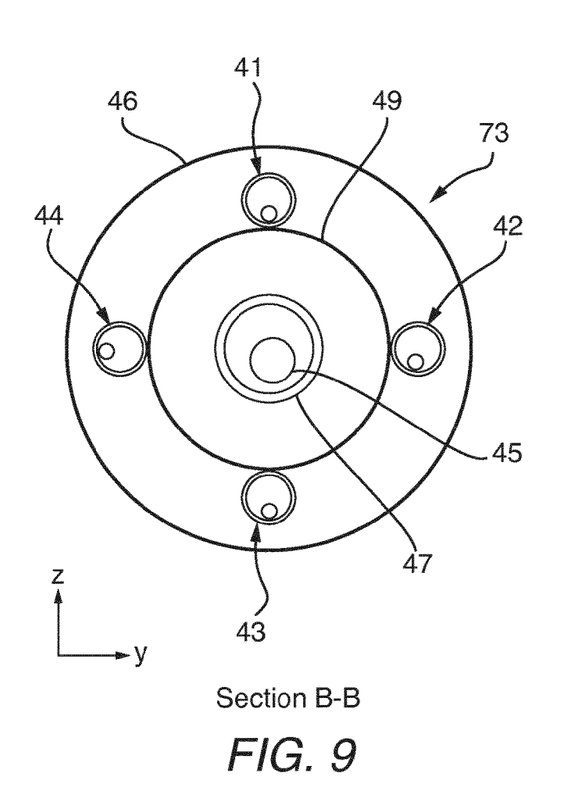
FIG. 9 is a schematic illustration of a cross section of a perfusion catheter according to an embodiment.

FIG. 8 shows a cross sectional view of the catheter 40 in the transverse plane A-A through the shaft 3, whereas FIG. 9 shows a cross sectional view of the catheter 40 in the transverse plane B-B through the balloons 46, 49. The shaft 3 has an outer diameter of 1.90 mm and an inner diameter of 1.66 mm, the GWL 47 has an outer diameter of 0.84 mm and an inner diameter of 0.69 mm, the return lumens of the cooling elements each have an outer diameter of 0.39 mm and an inner diameter of 0.35 mm, and the supply lumens each have an inner diameter of 0.09 mm.

The inner and outer balloons are preferably inflated at approximately the same time but alternatively either one may be inflated before the other. Referring to FIG. 8, an inner balloon inflation lumen 8 is adhered to the outside of GWL 47 using a solid glue filler (or equivalent sealing medium) 9. The glue filler 9, GWL 47 and inner balloon inflation lumen 8 form a body around which the flexible membrane of the inner balloon 49 is tightly wrapped. The four cooling elements 41, 42, 43, 44 are provided between the outside of the membrane of the inner balloon 49 and the inner surface of the shaft 3. The space inside the shaft 3 between the cooling elements 41, 42, 43, 44 and the inner balloon membrane 49 forms an outer balloon inflation lumen 4. The inner balloon inflation lumen 8 is configured to supply inflation fluid, in the form of a gas, for inflating the inner balloon 49 and, when inflated, receive said inflation fluid for deflating the inner balloon 49. Similarly, the outer balloon inflation lumen 4 is configured to supply inflation fluid, in the form of a liquid, for inflating the outer balloon 73 and receive said inflation fluid for deflating the outer balloon 73 when an operator adjusts the pressure. Alternatively separate inflation and deflation lumens may be provided for either or both of the inner and outer balloons.

Figure 10:
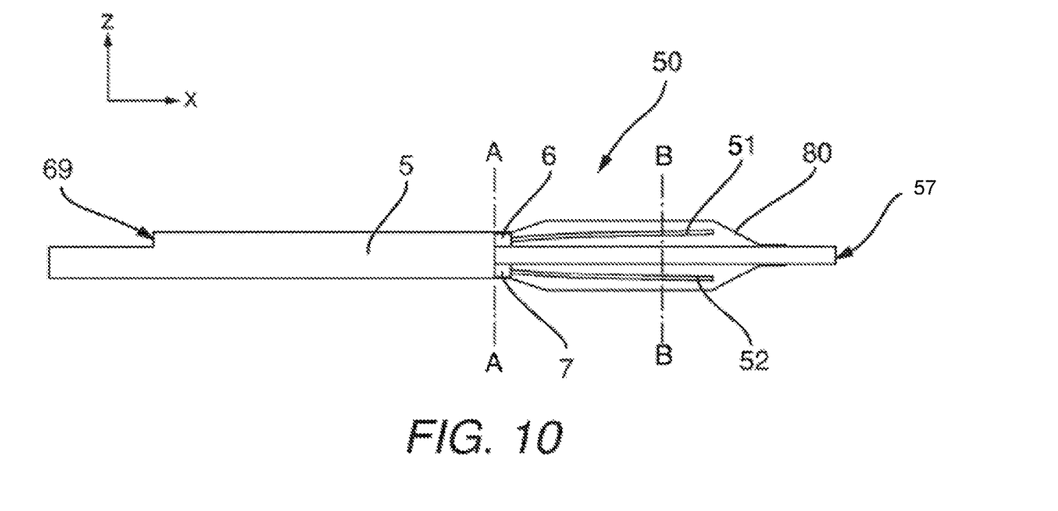
FIG. 10 is a schematic illustration of a perfusion catheter according to an embodiment.
Figure 11:
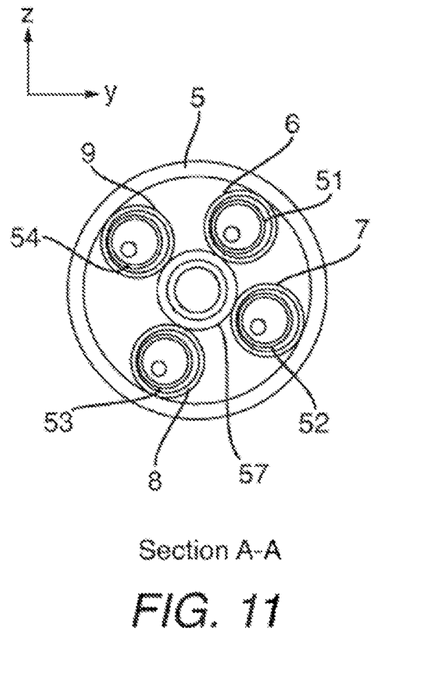
FIG. 11 is a schematic illustration of a cross section of a perfusion catheter according to an embodiment.
Figure 12:
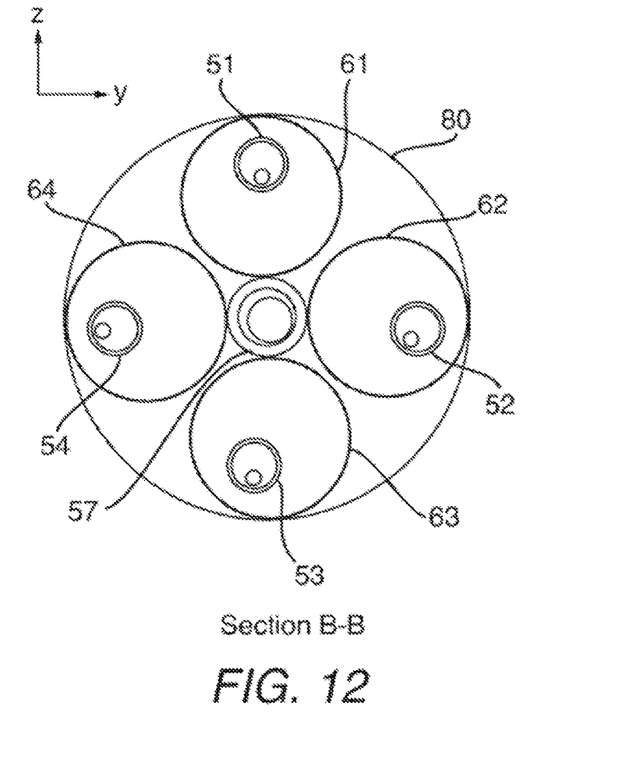
FIG. 12 is a schematic illustration of a cross section of a perfusion catheter according to an embodiment.

The inventors have also designed a further advantageous catheter 50 as shown in the embodiment of FIGS. 10 to 12.

In this embodiment a plurality of cooling elements 51, 52, 53, 54 are provided (as before) however each cooling element is provided within a separate cooling element balloon 61, 62, 63, 64 formed of a respective inflatable flexible heat transfer membrane. Only two of four cooling elements 51, 52 are visible in FIG. 10, with their respective cooling element balloons 61, 62 in FIG. 12. Each of the cooling element balloons 61, 62, 63, 64 is inflated using an inflation fluid, which is typically a sterile fluid such as saline. The cooling element balloons 61, 62, 63, 64 are substantially cylindrical (as shown in FIG. 12) however they are tapered at their distal ends, towards the central GWL 57, as shown by FIG. 10. Each cooling element balloon 61, 62, 63, 64 is shaped to form a quarter segment of a whole artery occlusion balloon.

The cooling element balloons 61, 62, 63, 64 are bound together by an elasticated member 80 in the form of a membrane which fully encloses the cooling element balloons 61, 62, 63, 64 to provide a sealed volume inside. The elasticated member 80 preferably has good heat transfer properties so as to allow the transfer of heat between the cooling element balloons 61, 62, 63, 64 and the surrounding bodily tissue. A sterile fluid may be provided between the inside of the elasticated member 80 and the cooling element balloons 61, 62, 63, 64 to improve thermal communication between the cooling element balloons 61, 62, 63, 64. Alternatively however the elasticated member 80 may be vacuum fitted to the outside of the cooling element balloons 61, 62, 63, 64. Furthermore, in an alternative example the elasticated member 80 may only partially extend the outside of the cooling element balloons 61, 62, 63, 64, or comprise an elasticated mesh (for example) which holds the cooling element balloons 61, 62, 63, 64 in a desired arrangement. Most preferably each cooling element balloon 61, 62, 63, 64 extends in the same direction and is touching at least one adjacent cooling element balloon when said cooling element balloons are inflated.

FIG. 11 shows a cross sectional view which has been taken through the transverse plane A-A of the main shaft 5. The cooling elements 51, 52, 53, 54 each have a respective cooling element shaft 6, 7, 8, 9 onto which the membrane for the respective cooling element balloon is adhered. The cooling element shafts 6, 7, 8, 9 protrude slightly from the main shaft 5, as illustrated in FIG. 10. Each cooling element shaft 6, 7, 8, 9 also behaves as an inflation and deflation lumen for the respective cooling element balloon, using the volume between the outside of the cooling element and the inner wall of the cooling element shaft, as previously described. These cooling element shafts 6, 7, 8, 9 may combine together into a common conduit at a proximal end of the catheter for simplified delivery or removal of inflation fluid. Alternatively, control of inflation and deflation of each of the cooling element balloons 61, 62, 63, 64 may be achieved on an individual basis, using separate inflation fluid reservoirs. The cooling element shafts 6, 7, 8, 9 are arranged around the GWL 57 inside the main shaft 5. The main shaft 5 has an outer diameter of 1.90 mm and an inner diameter of 1.66 mm, whereas each cooling element shaft has an outer diameter of 0.55 mm and an inner diameter of 0.35 mm. The inner supply lumen in each of the cooling elements 51, 52, 53, 54 has an outer diameter of 0.12 mm and an inner diameter of 0.09. The GWL has an outer diameter of 0.59 mm and an inner diameter of 0.44 mm. The shafts, membranes, lumens and cooling elements described may be formed of any of the materials previously described and operate in a similar way.

In order to increase the rate of cooling at the tissue, the cooling elements 51, 52, 53, 54 each extend radially outward from the central axis of the catheter 50 (which is occupied by the GWL 57), and along said axis, such that they are disposed on the 'tissue side' of their respective balloons. This is clearly shown in FIG. 12, which shows a cross-sectional view through the balloons, along the transverse B-B plane. This may be achieved by any of the previous techniques discussed however most preferably is achieved by preforming the cooling elements 51, 52, 53, 54 with an inherent mechanical bias to extend outward and away from the central GWL 57.

In a similar manner to the embodiment of FIGS. 7 to 9, a particular benefit is provided wherein the GWL 57 also acts as a perfusion lumen which conveys bodily fluids, such as blood, from the guide wire exit aperture 69, along the central axis of the catheter 50 and to the guide wire entrance aperture 63. The arrangement of the cooling element balloons 61, 62, 63, 64 around the outside of the perfusion lumen 57 prevents the warm blood transported through the perfusion lumen 57 from significantly counteracting the cooling effect provided by the cooling element balloons 61, 62, 63, 64 at the tissue.

Figure 13:
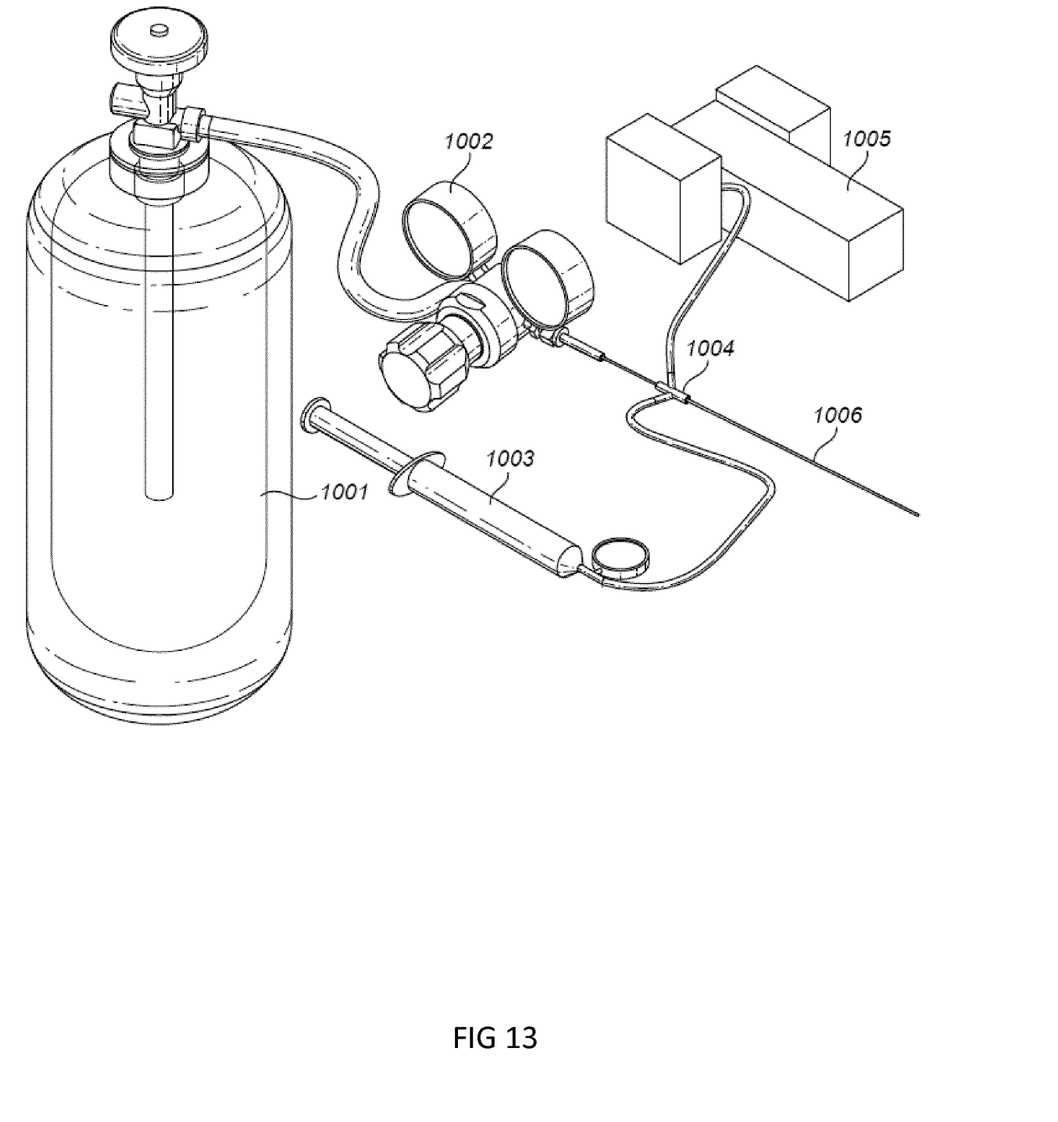
FIG. 13 is an illustration of a system for operating a catheter according to an embodiment.

FIG. 13 is an illustration of an exemplary system for using the catheter according to the embodiments described herein to cool a target part of a vessel. It will be understood that some of the specifically described components may not be essential to the operation of the system but are described for context only. Suitable, functionally similar, or equivalent components may be used interchangeably.

The system comprises:
Coolant cylinder 1001
Pressure regulator 1002
Tri-connector 1004
Vacuum pump 1005
Inflation device 1003
Catheter shaft 1006

Although not shown in FIG. 13, the system also comprises a catheter end according to any of the embodiments described herein.

The coolant cylinder 1001 has a dip tube and spigot valve for controlling the supply of the coolant. A flexible high pressure hose connects the coolant cylinder to the pressure regulator 1002. An injection tube from the pressure regulator connects to the tri-connector 1004. Also connected to the tri-connector is an inflation tube connected to inflation device 1003 and a vacuum tube connected to the vacuum pump 1005. The tri-connector maintains the injection tube, the vacuum tube and the inflation tube as separate from each other. The tri-connector also connects to the catheter shaft 1006 and thereby supports fluid and/or gas communication between the catheter and the coolant supply, vacuum pump, and inflation device.

The system may also include a heat exchanger, not shown in FIG. 13, to cool the liquid coolant before it enters the catheter. This will prevent boiling of the coolant as it enters the warm environment of the patient's body. Heat may be removed from the liquid coolant by using a refrigeration circuit or Peltier cooler.

The system may further comprise a computer, such that the system may be software controlled, the computer having one or more controls and/or a user interface such as a graphical user interface. The system may also further include assemblies for temperature and/or pressure monitoring based on signals received from one or more sensors.

The inflation device 1003 operates by causing an inflation fluid to flow into the catheter shaft 1006 when the plunger is pressed. The inflation device is also a deflation device since the inflation fluid flows back into the device from the catheter when the plunger is withdrawn. The inflation device may alternatively be an electric pump.

The vacuum pump 1005, that may be an electric vacuum pump, operates on the return lumens of the coolant. The vacuum pump 1005 advantageously lowers the pressure in the return lumen and/or cooling chamber of the cooling elements to thereby increase the amount of phase change of the coolant that occurs. The vacuum pump 1005 also ensures that the coolant in the supply lumens and cooling chambers (where provided) flows into the return lumen.

A further advantage applying the vacuum pump 1005 to the return lumens is that the pressure in the return lumen is relatively low and less than typical blood pressure in a body. In use, should the return lumens leak, this would result in blood flowing into the return lumens rather than the coolant flowing out. The vacuum pump 1005 thereby improves the safety of the catheter.

The catheter shaft 1006 in the system shown in FIG. 13 may be any of the catheter shafts discussed herein.

The system may also comprise a deflation device, separate from the inflation device 1003, that is in fluid communication with the catheter shaft 1006 through an additional separate connection to the tri-connector. The deflation device may be a vacuum pump, such as an electric vacuum pump.

Variables that influence the operation of the catheter are the pressure of the inflated balloon and the temperature of the outer surface of the balloon. Both of these are controllable by how the system of FIG. 13 is operated. The pressure of the balloon is controllable by controlling the amount, and pressure of, the inflation fluid by inflation device 1003. The temperature of the outer surface of the balloon is dependent on both the temperature of the cooling element and how long the cooling element has been cooling the inflation fluid. The temperature of the cooling element is controllable by controlling the pressure and the amount of coolant that flows into the catheter. The length of time that the inflation fluid is cooled by the cooling element is easily controlled by when the system operator starts the flow of the coolant into the catheter and removes the catheter.

Preferably, the pressure of the balloon is maintained at lower than 5 ATM (507 kPa) and may more preferably be as low as 3 ATM (304 kPa) or 1 ATM (101 kPa). It may be desirable for the balloon pressure to be as low as possible for effective treatment in order to mitigate the risk of a reaction occurring in the blood vessel that leads to re-stenosis or blockage. A short-term response to the application of high-pressure cryotherapy is also often smooth muscle cell proliferation, which is potentially dangerous. The tissue interface temperature is preferably maintained within a desired range in order to remove heat from the plaque and vessel without significantly ablating the cells. It is noted that throughout the present document, all pressures given as gauge pressures, that is, above atmospheric pressure.

The temperature of the outer surface of the balloon is maintained within appropriate ranges given the application. For example, for cryotherapy, the temperature is preferably maintained between +15° C. (288K) and −35° C. (238K) and more preferably between 0 to −30° C. (273K to 243K). For atrial fibrillation (and other applications where tissue ablation is required) the temperature may be much lower, for example between −50° C. to −90° C. (223K to 183K), although typically around −80° C. (193K).

The exact temperature will depend on the treatment application, according to standard practice. Depending on the type of balloon and the heat load, there may be a temperature difference of about 10° C. to 40° C. between inner and outer balloon temperature and this can be compensated for when controlling the system.

Preferably, sensors are provided within, on or near the catheter end, such as on or just inside the balloon, in order to monitor and thereby control the temperatures and pressures in a feedback control system. For example, a thermocouple may be fixed to the GWL to measure the temperature inside the balloon. One or more further thermocouples may be attached to the internal or external surface of the balloon in order to measure the balloon tissue interface temperature. In addition, a pressure sensor may be placed inside the balloon to accurately monitor and thereby control the pressure within the balloon. The pressure sensor may be an open hydraulic tube with no flow, or may be positioned on the inflation circuit near the inflator, so that the fluid pressure inside the tube is measured outside the catheter. The pressure sensor may also be a piezoelectric transducer, fibre-optic transducer or other type of sensor.

Pressure sensors and a flow meter may also be positioned in the coolant circuit, to measure the pressure and flow of the coolant.

Both temperature and pressure signals can be used to control refrigerant flow such that balloon pressure and surface temperature remain within the desired ranges. The pressure transducer may also be used to detect any leaks within the catheter by sensing abnormal pressures. The temperature sensor(s) may also be used to detect vessel occlusion by the balloon.

As described earlier, the catheter may also comprise means for heating the inflation fluid, or solidified inflation fluid, within the balloon. Advantageously, this allows frozen inflation fluid to be thawed quickly if required.

In order to support the sensors, means for heating and any other devices at the distal end of the catheter, the system may further comprise connectors to one or more power supplies, data interfaces, or other signal processing units, configured to provide a power supply, control signals and to convert sensor signals into data. Electrical wires may be housed in the catheter shaft together with the lumens or along the outside of the catheter shaft.

Preferably, the volume of the inflation fluid is fixed and small. This minimises the damage caused by any leakage. The injection of the inflation fluid to inflate the balloon may be automatically controlled and performed, for example, by an operator pressing a button. Alternatively, the inflation fluid may be injected manually.

According to known techniques, one or more portions of the catheter may be radiopaque and/or include a radiopaque marker. This aids the operator of the catheter.

The cooling elements are characterized supply lumen provided inside a return lumen. The supply lumen may be positioned centrally within the return lumen but this is not essential. The supply lumen may alternatively lie along a side of the return lumen or be in no way fixed to the return lumen so that its position within the return lumen can change.

Embodiments include the use of any number of cooling elements so long as there is more than one cooling element. Providing two cooling elements is advantageous over a catheter with a single cooling element because faster cooling can be achieved. Increasing the number of cooling elements further increases the rate of cooling and also further improves the uniformity of the cooling over the balloons surface. In particular, the number of cooling elements according to embodiments may be two, three, four, five, six, or more.

Further embodiments include a number of modifications and variations that can be made to the embodiments as described above. In particular, all of the dimensions provided in the figures are approximate and embodiments include catheter designs with different dimensions. Furthermore the dimensions may also vary depending on the size of the human or animal that is being treated. Throughout the present document various features are described as lumens and tubes. These terms may be used interchangeably and said features may also be referred to as conduits.

In the above-described operation of the system, operational temperatures and pressures are provided. However, embodiments are in no way limited to these operational temperatures and pressures. Moreover, the operational temperatures and pressures may be varied depending on the application. In particular, embodiments include the catheter, and the system supporting the catheter, being operated according to the disclosure in WO 2012/140439 A1, the entire contents of which are incorporated herein by reference.

Other embodiments of the invention will be apparent to those skilled in the art from consideration of the specification and practice of the embodiments disclosed herein. It is intended that the specification and examples be considered as exemplary only, with a true scope and spirit of the invention being indicated by the following claims. In addition, where this application has listed the steps of a method or procedure in a specific order, it may be possible, or even expedient in certain circumstances, to change the order in which some steps are performed.

The invention claimed is:

1. A catheter comprising:
   a flexible heat transfer element provided on an outer surface of the catheter;
   a first conduit arranged to supply an inflation fluid for inflating the flexible heat transfer element so as to form an inflated outer balloon; and
   an inner balloon, coaxially arranged with the inflated outer balloon;
   a second conduit arranged to supply an inflation fluid for inflating the inner balloon;
   a plurality of cooling elements arranged to cool said inflation fluid for inflating the outer balloon;
   wherein each cooling element comprises a first tube provided inside a second tube, wherein the first tube is substantially parallel to the second tube;
   wherein the second tube is configured to receive a flow of a coolant for cooling the cooling element from the first tube;
   wherein each cooling element comprises an elongate cooling chamber configured to receive coolant from the first tube and provide said coolant to the second tube;
   wherein each of the cooling elements is arranged on an outer surface of the inner balloon; and
   wherein, when the inner balloon and the outer balloon are inflated, the cooling elements are spaced from an inner surface of the outer balloon.

2. The catheter according to claim 1, wherein the cooling elements are arranged within the catheter so that the inner surface of the outer balloon is cooled substantially uniformly.

3. The catheter according to claim 1, wherein said cooling elements are elongate and arranged parallel to one another.

4. The catheter according to claim 3, wherein each cooling element has substantially the same lateral spacing from an axis of the outer balloon parallel to the cooling elements.

5. The catheter according to claim 1, wherein, as viewed in the plane normal to the longitudinal axis of the cooling elements and relative to the center of the outer balloon, each of a plurality of the cooling elements is separated from an adjacent cooling element by a substantially equal angle.

6. The catheter according to claim 1, wherein said cooling elements are configured such that, when the flexible heat transfer element is inflated, a spacing between the cooling elements is larger than when the outer balloon is not inflated.

7. The catheter according to claim 1, wherein said plurality of cooling elements comprises at least three cooling elements.

8. The catheter according to claim 1, wherein said catheter is a perfusion catheter further comprising a central perfusion lumen configured to convey a bodily fluid along the center of the catheter, wherein said cooling elements are arranged around said perfusion lumen.

9. The catheter according to claim 1 wherein, in use in a vessel, the inflated flexible heat transfer element occludes fluid flow between the walls of the vessel and the inflated flexible heat transfer element.

10. The catheter according to claim 1, wherein said plurality of cooling elements are provided inside the flexible heat transfer element.

11. The catheter according to claim 1, wherein, in use, the first tube and the second tube are operated such that the pressure of the second tube is lower than the first tube.

12. The catheter according to claim 1, wherein for each cooling element, the elongate cooling chamber is arranged co-linearly with an end of the second tube.

13. The catheter according to claim 1, wherein each cooling element further comprises a restriction tube configured to convey the coolant from the first tube to the cooling chamber, wherein said restriction tube has narrower internal diameter than the first tube.

14. The catheter according to claim 13, wherein the restriction tube and cooling chamber are configured such that when the coolant conveyed along the first tube is a liquid, at least some of the coolant undergoes a phase change in the restriction tube and/or in the cooling chamber and returns through the second tube as a gas.

15. The catheter according to claim 1, wherein the first conduit is further configured to provide a return flow of the inflation fluid of the flexible heat transfer element.

16. The catheter according to claim 1, further comprising a guide wire lumen, wherein each of the cooling elements is not attached to an end of the guide wire lumen and wherein each cooling element is configured such that, when in use, the flow of the coolant causes the cooling element to vibrate.

17. The catheter according to claim 1, wherein each cooling element is configured such that, when the outer balloon is inflated, each cooling element is configured to at least partially have a helical shape.

18. A catheter comprising:
   a plurality of heat transfer elements, wherein each heat transfer element is flexible and is configured to be inflated with an inflation fluid so as to form a respective cooling element balloon;
   wherein each cooling element balloon comprises a cooling element arranged to cool said inflation fluid;
   wherein each cooling element comprises a first tube provided inside a second tube, wherein the first tube is substantially parallel to the second tube; and the second tube is configured to receive a flow of a coolant for cooling the cooling element from the first tube,
   wherein the cooling element balloons are elongate and extend along a common axis; and
   wherein the cooling element balloons are laterally displaced from each another in a direction perpendicular to the common axis.

* * * * *